United States Patent [19]

De Thomas et al.

[11] 4,153,578

[45] May 8, 1979

[54] CATALYST COMPRISING RANEY NICKEL WITH ADSORBED MOLYBDENUM COMPOUND

[75] Inventors: Waldo R. De Thomas, Parsippany; Eugene V. Hort, Wayne, both of N.J.

[73] Assignee: GAF Corporation, New York, N.Y.

[21] Appl. No.: 929,253

[22] Filed: Jul. 31, 1978

[51] Int. Cl.² .................. B01J 23/64; B01J 23/88; B01J 25/02; B01J 27/24

[52] U.S. Cl. .................. 252/438; 252/469; 252/470; 252/477 Q; 568/861

[58] Field of Search .......... 252/438, 469, 470, 477 Q; 568/861

[56] References Cited

U.S. PATENT DOCUMENTS

| | | | |
|---|---|---|---|
| 2,948,687 | 8/1960 | Hadley | 252/477 Q |
| 2,953,605 | 9/1960 | Hort et al. | 568/861 |
| 4,048,116 | 9/1977 | Voges et al. | 568/861 |

*Primary Examiner*—W. J. Shine
*Attorney, Agent, or Firm*—Walter C. Kehm; Walter Katz

[57] ABSTRACT

This invention provides an improved Raney nickel catalyst characterized by having a molybdenum compound adsorbed thereon. The novel catalyst contains about 0.5–15 parts by weight of molybdenum adsorbed per 100 parts by weight of Raney nickel solids. Optionally, one or more additional metals may be included in the catalyst. The catalyst is particularly effective in the manufacture of high quality butanediol by hydrogenation of butynediol, and for selective hydrogenation of carbonyl groups, sometimes even in the presence of carbon-carbon unsaturation, e.g. for the conversion of furfural to furfuryl alcohol.

9 Claims, No Drawings

CATALYST COMPRISING RANEY NICKEL WITH ADSORBED MOLYBDENUM COMPOUND

BACKGROUND OF THE INVENTION

1. Field of the Invention

This invention relates to Raney nickel catalysts modified by molybdenum, and, more particularly, to new and improved Raney nickel catalysts activated by a molybdenum compound which is adsorbed on the Raney nickel solids.

2. Description of the Prior Art

Raney nickel is a well known hydrogenation catalyst which was described originally in U.S. Pat. No. 1,638,190, and in J.A.C.S. 54, 4116 (1932). Raney nickel is prepared by alloying nickel and aluminum and leaching out the aluminum with alkali to expose the nickel as a finely divided, porous solid in which form nickel is an effective hydrogenation catalyst.

Subsequently, improved Raney nickel catalysts have been provided in the art by alloying various metallic constituents with the nickel and aluminum prior to treatment with alkali. For example, in U.S. Pat. No. 2,948,687 and in the Bull. Soc. Chim. (1946), p. 208–211, molybdenum is alloyed with nickel and aluminum and treated with alkali to provide a nickel-molybdenum alloy catalyst. However, such nickel-molybdenum alloy catalysts are not as effective as the catalysts of this invention for use as hydrogenation catalysts, e.g. of butynediol, particularly with respect to the quality of the product obtained.

Accordingly, it is the object of this invention to provide an improved Raney nickel catalyst which performs effectively in different catalytic hydrogenation processes.

SUMMARY OF THE INVENTION

This invention provides an improved Raney nickel catalyst characterized by having a molybdenum compound adsorbed on the Raney nickel surface. The novel catalyst contains about 0.5–15 parts by weight of molybdenum adsorbed per 100 parts by weight of the Raney nickel solids in the catalyst. Optionally, one or more additional metals, such as copper, cobalt, tungsten, zirconium, platinum or palladium may be included in the catalyst. The novel catalyst is prepared by mixing a liquid suspension of Raney nickel with a molybdenum compound whereby the molybdenum compound is adsorbed by the solid particles.

The catalyst of the invention is particularly effective in the manufacture of high quality butanediol by hydrogenation of butynediol, for selective hydrogenation of carbonyl groups in the presence of unsaturated groups, e.g. for the conversion of furfural to furfuryl alcohol, and for hydrogenation of formaldehyde to methanol.

DESCRIPTION OF THE PREFERRED EMBODIMENT

In accordance with the present invention, the catalyst is prepared from Raney nickel solids which are suspended in a liquid medium, preferably in water. Then a suitable amount of a molybdenum compound is added to the suspension and the mixture is stirred so that the molybdenum compound can be adsorbed onto the Raney nickel solids.

Generally, the improved Raney nickel catalyst herein is prepared starting with commercially available Raney nickel, which is usually a suspension of about 50% by weight of nickel in water. The commercial slurry may be diluted, if desired, to provide a stirrable concentration of the Raney nickel for reaction with the molybdenum compound.

The suitable amount of the molybdenum compound is added as a solid, dispersion or a solution thereof to the Raney nickel suspension. Typical molybdenum compounds include various molybdenum salts and oxides, including ammonium and alkali molybdates, molybdic trioxide, and the like. Preferably the molybdenum compound is at least partially soluble in the liquid medium of the nickel suspension.

The mixture is then stirred at room temperature for a period of time which is sufficient to adsorb most of the molybdenum compound onto the Raney nickel solids. Usually about 10 minutes to 24 hours is suitable for this purpose, and about one hour generally is ample to adsorb the desired amount of the molybdenum compound onto the nickel solids. The resulting aqueous suspension may then be used as such as catalyst for a hydrogenation process. Any excess molybdenum compound present in suspension or solution does not interfere with the hydrogenation process, and, therefore, filtering of the catalyst suspension is unnecessary.

In accordance with the invention, suitably about 0.5–15 parts by weight of adsorbed molybdenum per 100 parts by weight of Raney nickel solids present is used as the catalyst composition. Preferably, about 2–8 parts by weight and, optimally, about 4 parts by weight molybdenum are used. In practice, the amount of molybdenum in the catalyst may be determined, after additions of known amounts of the molybdenum compound, by analysis of residual molybdenum still in suspension after stirring for given periods of time. Alternatively, the catalyst itself may be analyzed for nickel and molybdenum content.

As described in detail in copending application Ser. No. 924,212, filed July 12, 1978, (FDN-1113), the catalyst of the invention will produce high quality butanediol by a process involving a two-stage catalytic hydrogenation of a butynediol solution containing formaldehyde. During the first stage of the process, or low pressure, low temperature stage, a butanediol product having a much lower carbonyl number is obtained. The carbonyl number is the conventional measure of the undesired aldehyde and acetal content including residual formaldehyde. In the second or finishing stage, which is carried out at higher pressures and/or temperatures than the first stage, much less 2-methyl-1,4-butanediol byproduct (methylbutanediol) is produced concurrently with butanediol.

The results with the catalyst of the invention are very favorable and effective as compared to the results with untreated Raney nickel or with Raney nickel alloy catalysts containing molybdenum which was present in the Raney alloy before leaching. It is also more effective than Raney nickel with metals other than molybdenum adsorbed thereon.

A particular feature of the catalyst of the invention is its increased activity for reducing carbonyl groups sometimes even preferentially to carbon to carbon unsaturated groups in organic compounds which contain both groups. For example, furfural is reduced substantially to furfuryl alcohol by hydrogenation with the catalyst of this invention. On the other hand, Raney nickel itself, or Raney nickel from a molybdenum-containing alloy produces considerable amounts of tetrahydrofurfuryl alcohol byproduct.

The invention now will be illustrated with reference to the following specific examples, which are to be considered as illustrative, but not limiting of, the invention herein.

EXAMPLE 1

Adsorption of Molybdenum on Raney Nickel

To 10.0 g aliquots of Raney nickel solids in 40 ml of water were added various proportions of molybdenum in the form of ammonium molybdate. The suspensions were stirred at room temperature and, at intervals, filtered and the filtrates analyzed for molybdenum content. The following Table I gives the extent of adsorption of molybdenum as a function of time of stirring.

TABLE I

| Time | Ratio of Wt. of Mo to Wt. of Raney Ni Solids | | | | |
|---|---|---|---|---|---|
| | 0.03 | 0.04 | 0.06 | 0.08 | 0.12 |
| | % of Mo Charge Adsorbed on Catalyst | | | | |
| 10 min. | 86 | 83 | 78 | 75 | 73 |
| 1 hr. | 92 | 87 | 82 | 79 | 75 |
| 24 hrs. | 96 | 93 | 89 | 88 | 87 |

EXAMPLE 2

Preparation of Catalyst of Invention

To 20.0 g. of commercial Raney nickel containing about 50% nickel particles as an aqueous slurry was added solid ammonium molybdate, $(NH_4)_6Mo_7O_{24} \cdot 4H_2O$, and the mixture was stirred for an hour. The catalyst thus prepared then was added directly to the butynediol solution for use in the hydrogenation process.

Catalysts were prepared in this manner corresponding to 2, 3, 4, 5, 6 and 8 parts by weight of molybdenum added per 100 parts of Raney nickel solids.

EXAMPLE 3

Hydrogenation of Butynediol to Butanediol Raney Nickel (Control Experiment)

A. Low Pressure, Low Temperature Stage (First Stage)

500 g. of aqueous 35% butynediol solution containing 0.40% formaldehyde and a catalyst comprising 20 g. of commercial 50% Raney nickel slurry was hydrogenated under agitation at 60° C. and 300 psig of hydrogen. After 6 hours, the catalyst was allowed to settle and the supernatant product was withdrawn. Thereafter, another 500 ml. of 35% butynediol solution was added and the hydrogenation procedure was repeated. Four successive hydrogenations were run with the same catalyst; the results are given for the fourth run in the series.

The reaction product has a carbonyl number of 48 and a formaldehyde content of 0.22%.

B. High Pressure, High Temperature Stage (Finishing Stage)

The product of the low pressure stage was subjected to finishing hydrogenation over a 15% nickel—7.8% copper—0.5% manganese catalyst on alumina at 2500 psig, and 150° C. for 7.5 Hours. The reaction product, after removing water, then was totally distilled, and, the organics were collected up to a pot temperature of 180° C. at 1 Torr.

The distilled butanediol product had a carbonyl number of 0.3 and a 2-methyl-1,4-butanediol content of 2.0%.

EXAMPLE 4

Raney Nickel-Mo Alloy

The hydrogenation process of Example 3 was repeated using an alloy catalyst containing 3% by weight molybdenum prepared by alkali leaching of a nickel-molybdenum-aluminum alloy.

The butanediol product of the low pressure stage had a carbonyl number of 22 and a formaldehyde content of 0.16%. After the finishing stage, the carbonyl number was 0.3, and the methylbutanediol content was 1.6%.

EXAMPLE 5

Raney Nickel+Mo Compound Adsorbed

The hydrogenation process of Example 3 was repeated using the catalysts of the invention prepared according to Example 2.

The butandiol product of the first stage, for catalysts having added molybdenum content of 2, 3, 4, 5, 6 and 8 parts by weight of molybdenum gave corresponding carbonyl numbers of 9, 7, 5, 5, 6 and 6. The formaldehyde content of the products were 0.10%, 0.08%, 0.09%, 0.09%, 0.10% and 0.08%, respectively.

After the finishing stage the carbonyl numbers were, respectively, 0.3, 0.15, 0.1, 0.1, 0.15 and 0.2. The methylbutanediol contents were, respectively, 0.9%, 0.7%, 0.6%, 0.6% 0.6% and 0.5%.

EXAMPLE 6

Raney Nickel—Cr Alloy+Mo Compound Adsorbed

The hydrogenation process of Example 3 was repeated using a catalyst prepared according to Example 2 from a commercial Raney nickel-chromium alloy containing 3% by weight chromium in the alloy to give a resultant catalyst having 4 parts of molybdenum adsorbed per 100 parts of Raney nickel solids.

The carbonyl number was 4.5 and the formaldehyde content was 0.10% in the low pressure stage. The carbonyl number was 0.1 and the methylbutanediol content was 0.6 after finishing.

EXAMPLE 7

Raney Nickel—Mo Alloy+Mo Compound Adsorbed

The hydrogenation process of Example 3 was repeated using a commercial Raney nickel-molybdenum alloy containing 3% by weight molybdenum which was treated as in example 2 to adsorb 4 parts of molybdenum per 100 parts of the alloy solids.

The carbonyl number was 17 and the formaldehyde content was 0.12% in the first stage; the carbonyl number was 0.3 and the methylbutanediol content was 1.2% after finishing.

EXAMPLE 8

Raney Nickel+Mo and Cu Compounds Adsorbed

A catalyst comprising 4 parts molybdenum compound adsorbed per 100 parts of Raney nickel solids was prepared as in Example 2, then an additional 4 parts of copper, as copper acetate, was dissolved in the butynediol solution, and the hydrogenation process of Example 3 was repeated.

The carbonyl number was 5 and the formaldehyde content was 0.09% in the low pressure stage. The carbonyl number was 0.2 and the methylbutanediol content was 0.6 after finishing.

EXAMPLE 9

Raney Nickel+Cu Compound Adsorbed

The hydrogenation process of Example 3 was repeated using a Raney nickel catalyst having about 6 parts of copper adsorbed per 100 parts of Raney nickel solids, as in U.S. Pat. No. 2,953,605. The carbonyl number was 37 and the formaldehyde content was 0.16% at the end of the first stage. After finishing the carbonyl number was 0.3 and the methylbutanediol content was 2.0%.

EXAMPLE 10

Hydrogenation of Furfural

Three identical hydrogenations were run using (A) unmodified Raney nickel (B) Raney Nickel containing 3% molybdenum alloyed as in the prior art, and (C) Raney nickel containing about 4 parts by weight molybdenum adsorbed per 100 parts of Raney nickel solids according to this invention.

In each hydrogenation, 175 g of furfural in 325 g. aqueous isopropyl alcohol was catalyzed with 10.0 g of the catalyst. After hydrogenation at 60° C. and 300 psig for 6 hours, the following results were obtained.

TABLE II

| | Catalyst Used | | |
|---|---|---|---|
| | (A) | (B) | (C) |
| Components of Reaction Product | % of Component | | |
| Furfuryl Alcohol | 31.0 | 70.0 | 98.0 |
| Tetrahydrofurfuryl Alcohol | 51.9 | 25.8 | 1.6 |
| Tetrahydrofurfural | 7.4 | 0.9 | 0.0 |
| Furfural | 8.6 | 2.2 | 0.1 |
| Others | 1.1 | 1.1 | 0.3 |

EXAMPLE 11

Hydrogenation of Formaldehyde

Two identical hydrogenations were run using (A) unmodified Raney nickel and (B) Raney nickel containing about 4 parts of molybdenum absorbed per 100 parts of Raney nickel solids.

In each hydrogenation 7.25 g. of formaldehyde in 493 ml. of water was catalyzed with 10.0 g. of the catalyst. After hydrogenation at 60° C. and 3000 psig for 6 hours, the following results were obtained:

TABLE III

| | Carbonyl No. | % Formaldehyde |
|---|---|---|
| Initial Feed Solution Catalyst of Hydrogenation | 27.1 | 1.45 |
| Unmodified Raney nickel (A) | 7.0 | 0.36 |
| Molybdenum adsorbed on Raney nickel (B) | 0.5 | 0.01 |

What we claim is:

1. An improved Raney nickel catalyst comprising Raney nickel solids having adsorbed therein a molybdenum compound in an amount of about 0.5-15 parts by weight molybdenum per 100 parts of the Raney nickel solids.

2. A catalyst according to claim 1 wherein said amount of molybdenum is about 2-8 parts by weight.

3. A catalyst according to claim 1 wherein said amount of molybdenum is about 4 parts by weight.

4. A catalyst according to claim 1 which includes at least one additional metal selected from the group consisting of copper, cobalt, tungsten, zirconium, platinum and palladium.

5. A catalyst according to claim 4 wherein said metal is copper.

6. A catalyst according to claim 1 in which said catalyst is prepared by mixing a liquid suspension of Raney nickel with molybdenum compound, added as a solid, dispersion or solution thereof.

7. A catalyst according to claim 1 wherein said molybdenum compound is added as a molybdenum salt or oxide.

8. A catalyst according to claim 1 wherein said molybdenum compound is selected from an ammonium molybdate, an alkali molybdate and molybdenum trioxide.

9. A catalyst according to claim 6 wherein said liquid is water.